(12) United States Patent
Nanaumi et al.

(10) Patent No.: US 9,213,039 B2
(45) Date of Patent: Dec. 15, 2015

(54) STATE QUANTITY DISTRIBUTION MEASURING APPARATUS AND METHOD OF MEASURING STATE QUANTITY DISTRIBUTION OF SAMPLE

(75) Inventors: Hisataka Nanaumi, Kagawa (JP); Teruko Kawamoto, Kagawa (JP); Misayo Arimura, Kagawa (JP); Yukiko Bitou, Kagawa (JP)

(73) Assignee: Unicharm Corporation, Ehime (JP)

( * ) Notice: Subject to any disclaimer, the term of this patent is extended or adjusted under 35 U.S.C. 154(b) by 442 days.

(21) Appl. No.: 13/812,192

(22) PCT Filed: Sep. 16, 2011

(86) PCT No.: PCT/JP2011/071766
§ 371 (c)(1),
(2), (4) Date: Jan. 25, 2013

(87) PCT Pub. No.: WO2012/043423
PCT Pub. Date: Apr. 5, 2012

(65) Prior Publication Data
US 2013/0174652 A1 Jul. 11, 2013

(30) Foreign Application Priority Data
Sep. 29, 2010 (JP) ................................. 2010-219691

(51) Int. Cl.
*G01N 35/00* (2006.01)
*A61F 13/84* (2006.01)

(52) U.S. Cl.
CPC ................ *G01N 35/00* (2013.01); *A61F 13/84* (2013.01); *A61F 2013/8488* (2013.01); *A61F 2013/8491* (2013.01)

(58) Field of Classification Search
CPC ............ A61F 13/84; A61F 2013/8491; A61F 2013/8488; G01N 35/00; G01N 33/246; G01N 25/56; G01N 27/223; G01N 19/10; G01N 27/048; G01N 9/36; G01N 5/00

USPC ............................ 73/335.04, 29.02, 73, 29.05
See application file for complete search history.

(56) References Cited

U.S. PATENT DOCUMENTS

| | | | |
|---|---|---|---|
| 3,214,845 | A | 11/1965 | Huffman |
| 4,748,400 | A | 5/1988 | Typpo |

(Continued)

FOREIGN PATENT DOCUMENTS

| | | |
|---|---|---|
| CN | 1213529 A | 4/1999 |
| JP | 3-99372 | 10/1991 |

(Continued)

OTHER PUBLICATIONS

Stic Search Report.*

(Continued)

*Primary Examiner* — Hezron E Williams
*Assistant Examiner* — Marrit Eyassu
(74) *Attorney, Agent, or Firm* — Brinks Gilson & Lione (57) ABSTRACT

A state quantity distribution measuring apparatus that allows easy measurement of a state quantity distribution in an absorbent article that has irregularities. The state quantity distribution measuring apparatus comprises a sensor selected from the group consisting of a moisture sensor, a humidity sensor, a temperature sensor, a heat flow rate sensor and a wind speed sensor, which measures a state quantity of a sample, a sample stage on which a sample to be measured, consisting of an absorbent article, is placed, and which has a raised surface for placing the sample thereon, a support mechanism which supports the sensor such that the contact pressure of the sensor with respect to the sample is essentially constant, a moving mechanism which moves either or both the sensor and the sample so that the sensor moves relative to the sample, and a measuring mechanism that measures a state quantity of the sample at multiple locations using the sensor/while moving the sensor relative to the sample by controlling the moving mechanism, thereby measuring the state quantity distribution of the sample.

10 Claims, 6 Drawing Sheets

(56) References Cited

U.S. PATENT DOCUMENTS

| | | | |
|---|---|---|---|
| 4,791,353 A * | 12/1988 | Typpo | 324/667 |
| 5,891,306 A | 4/1999 | Chase et al. | |
| 6,369,588 B1 | 4/2002 | Sleefe et al. | |
| 2002/0058128 A1 | 5/2002 | Toyoshima et al. | |
| 2003/0060112 A1 | 3/2003 | Rezai et al. | |
| 2004/0230172 A1 | 11/2004 | Shapira | |
| 2005/0147798 A1 | 7/2005 | Toyoshima et al. | |
| 2007/0264489 A1 | 11/2007 | Sasabe et al. | |
| 2011/0241706 A1 * | 10/2011 | Norton et al. | 324/686 |

FOREIGN PATENT DOCUMENTS

| | | |
|---|---|---|
| JP | A-H09-290000 | 11/1997 |
| JP | 10-160784 A | 6/1998 |
| JP | A-H11-174015 | 7/1999 |
| JP | A-2002-165830 A | 6/2002 |
| JP | 2006-504976 A | 2/2006 |
| JP | A-2006-52159 | 4/2006 |
| JP | 2007-078425 A | 3/2007 |
| JP | 2008-026140 A | 2/2008 |
| JP | 2009-178410 A | 8/2009 |
| TW | 200615322 A | 5/2006 |
| WO | WO 99/12024 | 3/1999 |
| WO | WO 2004/060244 A1 | 7/2004 |

OTHER PUBLICATIONS

International Search Report based on corresponding PCT application No. PCT/JP2011/071766 dated Dec. 27, 2011 (2 pgs).

* cited by examiner

STATE QUANTITY DISTRIBUTION MEASURING APPARATUS AND METHOD OF MEASURING STATE QUANTITY DISTRIBUTION OF SAMPLE

RELATED APPLICATION

This application is a 35 U.S.C. §371 national phase filing of International Patent Application No. PCT/JP2011/071766, filed Sep. 16, 2011, through which and to which priority is claimed under 35 U.S.C. §119 to Japanese Patent Application No. 2010-219691, filed Sep. 29, 2010.

TECHNICAL FIELD

The present invention relates to a state quantity distribution measuring apparatus, and to a method of measuring a state quantity distribution of a sample.

BACKGROUND ART

An important step in the development of an absorbent article, for product improvement, is performing appropriate evaluation of the distribution of state quantities, such as the distribution of moisture, distribution of humidity or distribution of temperature, on the absorption surface within specific regions of the absorbent article, when a liquid has been absorbed.

For example, experience in regard to the feeling of wetness in an absorbent article indicates that the wearer does not feel wetness in proportion to the total amount of liquid absorbed by the absorbent article, but rather tends to feel wetness in proportion to the amount of moisture remaining on the very top of the absorption surface of the absorbent article. This is because liquids absorbed inside the absorbent article, and especially in the absorber, do not readily seep out of the absorbent article even when pressure, such as body pressure, is applied. It is therefore important to appropriately evaluate state quantity distributions in specific regions of the absorbent article.

Figure 8:
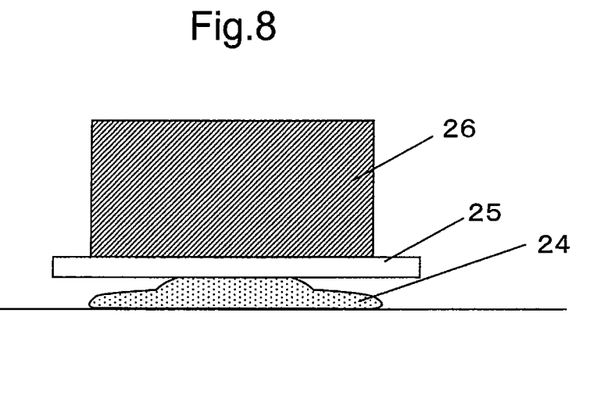
FIG. 8 is a diagram illustrating a conventional method of measuring moisture content in an absorbent article.

However, when the moisture content on the absorption surface of an absorbent article, for example, is to be evaluated, the method currently employed in the technical field involves, as shown in FIG. 8, dropping a liquid, such as artificial excreted fluid onto an absorbent article 24, placing an absorbent sheet 25, such as filter paper or tissue on the horizontally positioned absorbent article, applying a constant load by a weight 26 set on the absorbent sheet, and then measuring the amount of liquid that has migrated into the absorbent sheet after a prescribed period of time (PTLs 1-3).

In this evaluation method, however: (1) irregularities in the absorption surface of the absorbent article create sections that contact the absorbent sheet and sections that do not contact it, while the applied pressure also differs for different sections of the absorption surface. The inability to measure potentially skin-contacting regions in a comprehensive and consistent manner has therefore been a problem. Additional problems encountered with this evaluation method include that: (2) migration of liquid depends on the absorption power of the absorbent sheet, and the large variation in the absorbancy of different absorbent sheets leads to significant measurement error, and (3) the low amount of migration of liquid into the absorbent sheet also leads to significant measurement error. Furthermore, this evaluation method does not allow measurement of state quantity distributions in specific regions of the absorbent article.

Measurement of a state quantity in a specific region of an absorbent article can be accomplished using a sensor, such as a moisture sensor, humidity sensor, temperature sensor, heat flow rate sensor or wind speed sensor.

However, since the absorption surface of an absorbent article will generally have irregularities, the distribution of a state quantity on the absorption surface of the absorbent article cannot be easily measured under consistent conditions, such as under constant pressure.

A moisture sensor, for example, may also be used to measure the moisture content on the absorption surface of an absorbent article, and known moisture sensors include electrical capacitance, infrared-absorbing, microwave and electrical resistance moisture sensors. Of these, electrical capacitance-type moisture sensors are considered most suitable for measurement of moisture contents in specific regions of absorbent articles.

CITATION LIST

Patent Literature

[PTL 1] Japanese Unexamined Patent Publication No. 09-290000
[PTL 2] Japanese Unexamined Patent Publication No. 2002-165830
[PTL 3] Japanese Unexamined Patent Publication No. 2006-512159
[PTL 4] Japanese Unexamined Patent Publication No. 11-174015

SUMMARY OF INVENTION

Technical Problem

Nevertheless, the moisture contents that can be measured by an electrical capacitance-type sensor, such as described in PTL 4, for example, are only low moisture contents, and for example, with the sensor described in PTL 4 it is assumed that the moisture content will be in the range of 0-50 mass %, as stated in claim 8, and it is known that measurement of high moisture content regions is generally difficult to accomplish with moisture sensors. One reason for the difficulty of measuring high moisture content regions with electrical capacitance-type sensors is that water adheres to the sensor, resulting in significant measurement error.

It is therefore an object of the present invention to provide a state quantity distribution measuring apparatus that allows easy measurement of a state quantity distribution in an absorbent article that has irregularities.

It is another object of the invention to provide a state quantity distribution measuring apparatus which allows easy measurement of the moisture content in high moisture content regions of an absorbent article that has irregularities, using an electrical capacitance-type moisture sensor.

Solution to Problem

As a result of diligent research directed toward solving the problems described above, the present inventors have completed this invention upon finding that the aforementioned problems can be solved by a state quantity distribution measuring apparatus, comprising a sensor selected from the group consisting of a moisture sensor, a humidity sensor, a temperature sensor, a heat flow rate sensor and a wind speed sensor, which measures a state quantity of a sample, a sample stage on which a sample to be measured, consisting of an absorbent article, is placed, and which has a raised surface for placing the sample thereon, a support mechanism which supports the sensor such that the contact pressure of the sensor with respect to the sample is essentially constant, a moving mechanism which moves either or both the sensor and the sample so that the sensor moves relative to the sample, and a measuring mechanism that measures a state quantity of the sample at multiple locations using the sensor, while moving the sensor relative to the sample by controlling the moving mechanism, thereby measuring the state quantity distribution of the sample.

Specifically, the present invention relates to the following aspects.

[Aspect 1]

A state quantity distribution measuring apparatus, comprising:

a sensor selected from the group consisting of a moisture sensor, a humidity sensor, a temperature sensor, a heat flow rate sensor and a wind speed sensor, which measures a state quantity of a sample, a sample stage on which a sample to be measured, consisting of an absorbent article, is placed, and which has a raised surface for placing the sample thereon, a support mechanism which supports the sensor such that the contact pressure of the sensor with respect to the sample is essentially constant, a moving mechanism which moves either or both the sensor and the sample so that the sensor moves relative to the sample, and a measuring mechanism that measures a state quantity of the sample at multiple locations using the sensor, while moving the sensor relative to the sample by controlling the moving mechanism, thereby measuring the state quantity distribution of the sample.

[Aspect 2]

The state quantity distribution measuring apparatus according to aspect 1, wherein the sensor is an electrical capacitance-type moisture sensor, and the state quantity distribution measuring apparatus further comprises an insulating film separate from the sensor and situated between the sensor and the sample, for covering of the sample.

[Aspect 3]

The state quantity distribution measuring apparatus according to aspect 2, wherein the sensor has a pair of electrodes situated parallel across a predetermined spacing.

[Aspect 4]

The state quantity distribution measuring apparatus according to any one of aspects 1 to 3, wherein the raised surface of the sample stage is a curved surface forming all or part of the side wall of a cylinder.

[Aspect 5]

The state quantity distribution measuring apparatus according to aspect 4, wherein the moving mechanism rotates the sample stage around the central axis of the cylinder, thereby moving the sensor relative to the sample.

[Aspect 6]

The state quantity distribution measuring apparatus according to aspect 4 or 5, wherein the moving mechanism moves the sample stage parallel to the central axis of the cylinder, thereby moving the sensor relative to the sample.

[Aspect 7]

The state quantity distribution measuring apparatus according to any one of aspects 1 to 6, wherein the support mechanism holds the sensor such that contact pressure acts in the vertical direction and the sensor is capable of up-down movement.

[Aspect 8]

The state quantity distribution measuring apparatus according to aspect 7, wherein the support mechanism is a balance.

[Aspect 9]

The state quantity distribution measuring apparatus according to any one of aspects 1 to 8, further having a display mechanism that displays measurement results.

[Aspect 10]

A method of measuring the state quantity distribution of a sample, comprising the steps of:

(a) providing a state quantity distribution measuring apparatus comprising the following:
 (i) a sensor selected from the group consisting of a moisture sensor, a humidity sensor, a temperature sensor, a heat flow rate sensor and a wind speed sensor, which measures a state quantity of a sample,
 (ii) a sample stage on which a sample to be measured, consisting of an absorbent article, is placed, and which has a raised surface for placing the sample thereon,
 (iii) a support mechanism which supports the sensor such that the contact pressure of the sensor with respect to the sample is essentially constant,
 (iv) a moving mechanism which moves either or both the sensor and the sample so that the sensor moves relative to the sample, and
 (v) a measuring mechanism, (b) placing the sample on the raised surface of the sample stage, (c) setting the sensor on the sample, and (d) measuring the state quantity distribution of the sample in which the measuring mechanism measures a state quantity of the sample at multiple locations using the sensor, while moving the sensor relative to the sample by controlling the moving mechanism.

[Aspect 11]

A method of measuring the state quantity distribution of a sample, comprising the steps of:

(a) providing a state quantity distribution measuring apparatus comprising the following:
 (i) an electrical capacitance-type moisture sensor which measures the moisture content of a sample,
 (ii) a sample stage on which a sample to be measured, consisting of an absorbent article, is placed, and which has a raised surface for placing the sample thereon,
 (iii) a support mechanism which supports the sensor such that the contact pressure of the sensor with respect to the sample is essentially constant,
 (iv) a moving mechanism which moves either or both the sensor and the sample so that the sensor moves relative to the sample,
 (v) a measuring mechanism, and
 (vi) an insulating film separate from the sensor and situated between the sensor and the sample, for covering of the sample, (b) placing the sample on the raised surface of the sample stage, (c) setting the insulating film on the sample, (d) setting the sensor on the sample so as to sandwich the insulating film therebetween, and (e) measuring the state quantity distribution of the sample, in which the measuring mechanism measures a state quantity of the sample at multiple locations using the sensor, while moving the sensor relative to the sample by controlling the moving mechanism.

[Aspect 12]

The method according to aspect 10 or 11, wherein the state quantity distribution measuring apparatus further comprises a display mechanism that displays measurement results.

Advantageous Effects of Invention

The state quantity distribution measuring apparatus of the invention allows easy measurement of a state quantity distribution in an absorbent article.

The state quantity distribution measuring apparatus of the invention also allows easy measurement of the moisture content in high moisture content regions of an absorbent article that has irregularities, using an electrical capacitance-type moisture sensor.

DESCRIPTION OF EMBODIMENTS

The state quantity distribution measuring apparatus of the invention will now be explained in greater detail.

The state quantity distribution measuring apparatus allows measurement of a state quantity distribution in a sample that is to be measured, that comprises an absorbent article. There are no particular restrictions on the absorbent article, and examples include sanitary materials, such as disposable diapers, urine leakage-preventing sheets or urine-absorbing pads for incontinent patients and women's sanitary products, such as sanitary napkins and panty liners.

By appropriately selecting the sensor for the state quantity distribution measuring apparatus, it is possible to measure a state quantity in specific regions of the absorbent article, such as the liquid-permeable top sheet and especially on the uppermost surface, a state quantity inside the absorber, or a state quantity in the liquid-permeable back sheet.

Figure 1:
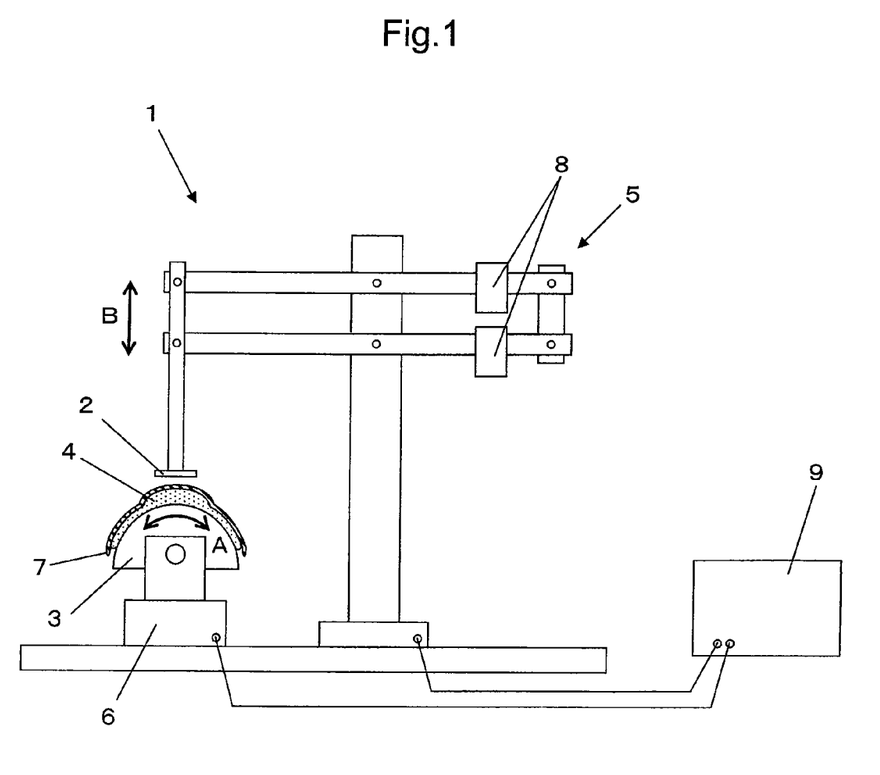
FIG. 1 is a diagram of the first embodiment of the state quantity distribution measuring apparatus of the invention.

FIG. 1 is an illustration of the first embodiment of the state quantity distribution measuring apparatus of the invention.

The state quantity distribution measuring apparatus 1 shown in FIG. 1 comprises a sensor 2 which measures a state quantity of a sample, a sample stage 3 on which a sample to be measured, consisting of an absorbent article, is placed, and which has a raised surface for placing the sample thereon, a support mechanism 5 which supports the sensor such that the contact pressure of the sensor with respect to the sample is essentially constant, a moving mechanism 6 which moves either or both the sensor and the sample so that the sensor moves relative to the sample, and a measuring mechanism 9 that measures a state quantity of the sample at multiple locations using the sensor, while moving the sensor relative to the sample by controlling the moving mechanism, thereby measuring the state quantity distribution of the sample.

In the state quantity distribution measuring apparatus 1 shown in FIG. 1, the sensor 2 is an electrical capacitance-type moisture sensor. Also, in the state quantity distribution measuring apparatus 1 shown in FIG. 1, the sample stage 3 has a half-regular cylinder shape formed by cutting a regular cylinder on a plane passing through the central axis. Also, in the state quantity distribution measuring apparatus 1 of FIG. 1, the support mechanism 5 is a balance capable of adjusting the load applied to the sample 4 by the location of a weight 8, and a constant load can be applied in the vertical direction indicated by B in FIG. 1 (hereunder also referred to as "direction B").

In addition, in the state quantity distribution measuring apparatus 1 shown in FIG. 1, the moving mechanism 6 can rotate the sample stage 3 around the central axis of the regular cylinder, along direction A, and can cause reciprocal movement of the sample stage 3 parallel to the central axis of the regular cylinder, i.e. in the direction from the foreground to the background in FIG. 1. By rotating the sample stage 3 in direction A and causing reciprocal movement of the sample stage 3 in the direction from the foreground to the background, the moving mechanism 6 allows a state quantity distribution of the sample to be evaluated.

Throughout the present specification, measurement of a state quantity distribution of the sample will also be referred to as "scanning" of the sample.

In the state quantity distribution measuring apparatus 1 shown in FIG. 1, the sensor 2 is connected via the support mechanism 5, and the moving mechanism 6 is directly connected to the measuring mechanism 9.

Also, in the state quantity distribution measuring apparatus 1 of FIG. 1, the sample 4 is set on the sample stage 3, and an insulating film 7 is placed between the sensor 2 and sample 4, covering the sample 4.

The procedure for measurement of the distribution of moisture content in the sample 4 in the state quantity distribution measuring apparatus 1 shown in FIG. 1 is as follows. First, the state quantity distribution measuring apparatus 1 shown in FIG. 1 is prepared. Next, the sample 4 is placed on the raised surface of the sample stage 3, the insulating film 7 is set on the sample 4, and the sensor 2 is set on the sample 4 sandwiching the insulating film 7 therebetween. The measuring mechanism 9 is then operated to control the moving mechanism 6, and the sample stage 3 is rotated in the direction A around the central axis of the regular cylinder of the sample stage 3 while the sample stage 3 is also moved in the direction from foreground to background. The sensor 2 is used during this time for measurement of the moisture content of the sample 4 at multiple locations. The moisture content distribution of the sample 4 can be measured by combining these measurements.

While not shown in FIG. 1, the state quantity distribution measuring apparatus 1 may also have a display mechanism, such as a monitor or printer that displays the measurement results. The display mechanism allows the measured results to be displayed in the form of a graph or the like.

The embodiment illustrated in FIG. 1 represents an example of an electrical capacitance-type moisture sensor, but, the sensor is not limited to an electrical capacitance-type moisture sensor and may be a non-electrical capacitance-type moisture sensor, such as an infrared-absorbing, microwave or electrical resistance moisture sensor. Also, the sensor is not limited to a moisture sensor and may instead be a humidity sensor, temperature sensor, heat flow rate sensor or wind speed sensor. A commercially available sensor may be used directly as an electrical capacitance, infrared-absorbing, microwave or electrical resistance moisture sensor, or a humidity sensor, temperature sensor, heat flow rate sensor or wind speed sensor.

When the sensor used in the state quantity distribution measuring apparatus is a moisture sensor, it is preferably an electrical capacitance-type moisture sensor as described above.

In regard to feeling of wetness in an absorbent article, the wearer tends to feel wetness in proportion to the amount of moisture remaining on the very top of the absorption surface of the absorbent article, and an electrical capacitance-type moisture sensor, due to its measuring principle, allows measurement of the moisture remaining on the very top of the absorption surface of the absorbent article.

Figure 2:
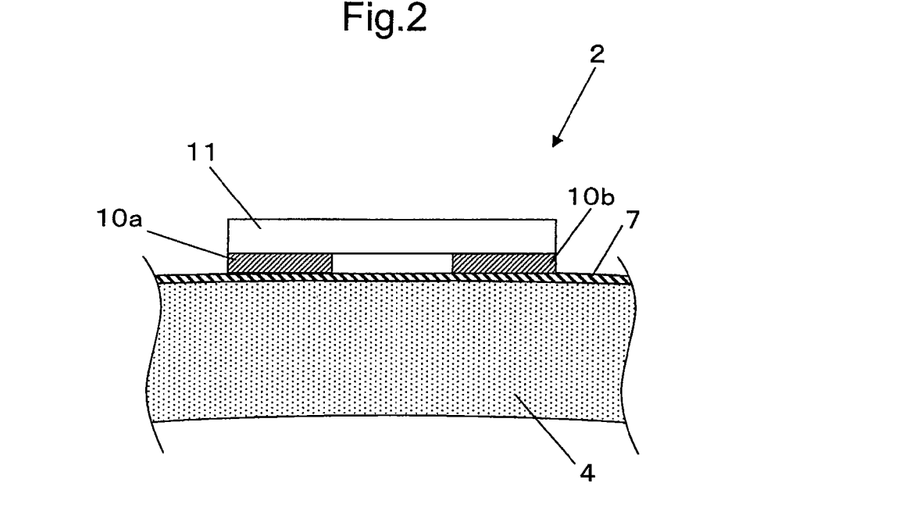
FIG. 2 is a diagram showing the positional relationship between a sensor 2 and a sample 4 during measurement of moisture content, as a state quantity.

When the sensor is an electrical capacitance-type moisture sensor, any commercially available electrical capacitance-type moisture sensor may be employed, as mentioned above, and the electrical capacitance-type moisture sensor may have a cross-sectional shape, such as shown in FIG. 2.

The sensor 2 shown in FIG. 2 has a pair of electrodes 10a and 10b situated parallel across a predetermined spacing. The electrostatic capacity between the pair of electrodes 10a and 10b is measured through a metal wire. The sensor 2 shown in FIG. 2 also comprises an electrode-supporting member 11 to support the pair of electrodes 10a and 10b. The sensor 2 shown in FIG. 2 has the pair of electrodes 10a and 10b mounted on the measuring side of the electrode-supporting member 11.

The electrode-supporting member preferably has a relative permittivity, water content and water permeability equivalent to the insulating film described hereunder, to avoid affecting measurement of the moisture content. An example of a material for the electrode-supporting member is phenol resin, known by trade names, such as BAKELITE.

While nothing is present between the pair of electrodes 10a and 10b in the sensor 2 shown in FIG. 2, according to a separate embodiment of the state quantity distribution measuring apparatus of the invention, the aforementioned electrode-supporting member may also be situated between the pair of electrodes 10a and 10b. By situating the electrode-supporting member between the pair of electrodes 10a and 10b, it is possible to maintain a more constant spacing between the electrodes and the sample.

The sensor 2 shown in FIG. 2 is in contact with the sample 4 through the insulating film 7. Since a load is applied in a constant vertical direction onto the sensor 2, the sensor 2 can measure the electrostatic capacity while a constant distance is maintained between the pair of electrodes 10a and 10b and the sample 4.

When the sensor is an electrical capacitance-type moisture sensor, the state quantity distribution measuring apparatus preferably comprises an insulating film separate from the sensor and situated between the sensor and the sample, for covering of the sample. The reason for this is as follows.

The absorption surface of an absorbent article, such as a disposable diaper, as the sample to be measured, often reaches a moisture content of nearly 100% after urination. When a moisture sensor is used to measure moisture content under such high moisture content conditions, part of the moisture will attach onto the sensor, especially near the electrodes, and can introduce error into the measurement results. Thus, placing an insulating film that is separate from the sensor between the sensor and the sample can prevent adhesion of moisture onto the sensor.

When the state quantity distribution measuring apparatus comprises such an insulating film, the sensor itself does not need to have an insulating section to retain the condenser properties of the electrodes, on the side in contact with the sample, as shown in FIG. 2. Also, the sensor may have an insulating section to retain the condenser properties of the electrodes on the side in contact with the sample, as in a known or commercially available electrical capacitance-type moisture sensor.

In terms of the attribute of measuring moisture content, the insulating film preferably has a ratio with respect to permittivity in a vacuum (hereunder referred to simply as "relative permittivity") of no greater than about 30, more preferably no greater than about 20, even more preferably no greater than about 10 and most preferably no greater than about 5. This is because a high relative permittivity can result in measurement error.

Also, the insulating film preferably has a small and uniform film thickness to reduce measurement error.

The film thickness is preferably no greater than about 300 μm, more preferably no greater than about 200 μm, even more preferably no greater than about 100 μm, yet more preferably no greater than about 50 μm and most preferably no greater than about 30 μm.

The uniformity is preferably such that the coefficient of variation of the film thickness measured at 30 arbitrary points is no greater than about 20%, more preferably no greater than about 10% and even more preferably no greater than about 5%.

The coefficient of variation is the value calculated by the following formula (1).

$$\text{Coefficient of variation (\%)} = 100 \times \text{standard deviation} / \text{arithmetic mean} \quad \text{Formula (1)}$$

The insulating film also preferably has a low water content to reduce measurement error. This is because a high water content will result in a high relative permittivity of the insulating film, and may increase measurement error.

As a general standard for the water content, the water content after immersion in water at 25° C. for 24 hours is preferably less than about 3 mass %, more preferably less than about 1 mass % and even more preferably less than about 0.5 mass %.

The insulating film preferably also has low water permeability. A general standard for low water permeability is a level such that the sensor and especially the electrodes are not wetted by water during measurement. This is because it may not be possible to accomplish measurement of the electrostatic capacity if the electrodes are wetted by water.

The material of the insulating film is not particularly restricted so long as it satisfies the performance described above, and examples include polyamide, melamine, epoxy, polyethylene, polypropylene, polyvinylidene chloride, polyvinyl chloride and polymethylpentene materials.

The state quantity distribution measuring apparatus, comprising the insulating film described above, can measure samples having moisture contents in a very wide range, such as preferably about 0 mass %-100 mass %, more preferably about 1 mass %-90 mass % and even more preferably about 5 mass %-80 mass %.

The insulating film can also be applied to sensors other than electrical capacitance-type moisture sensors, so long as it does not adversely affect the measurement. By using the insulating film it is possible to reduce measurement error caused by adhesion of moisture to sensors.

The sample stage 3 has a half-regular cylinder shape in the state quantity distribution measuring apparatus shown in FIG. 1, but, the shape of the sample stage is not limited to a half-regular cylinder and is not particularly restricted so long as it has a raised surface for placing the sample.

For example, when the sample is an absorbent article having irregularities on the surface to be measured, placing the sample on a sample stage with a raised surface will cause the measuring surface of the absorbent article to warp along the raised surface of the sample stage, thus allowing the contact area between the sensor and the sample to be reduced and minimizing the effects of the irregularities of the sample, to allow smooth measurement of the state quantity distribution. The raised surface of the sample stage is preferably a surface that maintains a constant contact area between the sample and the electrodes of the sensor.

The raised surface may be, for example, one that forms all or part of the side wall of a cylinder.

Throughout the present specification, the term "cylinder" includes regular cylinders that have a circular cross-section, elliptic cylinders that have an elliptical cross-section, approximately circular cylinders having an approximately circular cross-section, and approximately elliptic cylinders that have an approximately elliptical cross-section.

Figure 3:
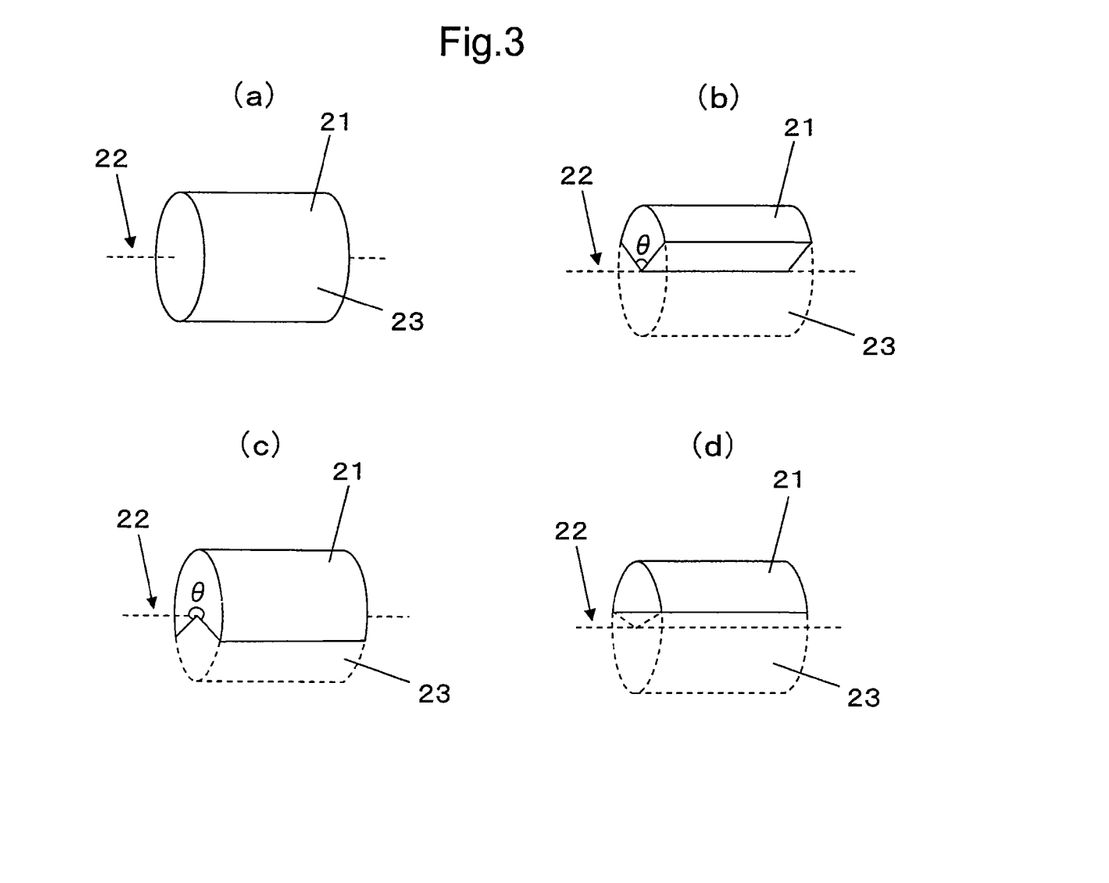
FIG. 3 is a set of diagrams showing examples wherein the raised surface is a curved surface composing all or part of the side wall of a regular cylinder.

FIG. 3 shows different examples of sample stages wherein the raised surface is a curved surface composing all or part of the side wall of a regular cylinder. FIG. 3(a) is an example wherein the raised surface 21 is the curved surface composing the entirety of the side wall 23 of a regular cylinder. Numeral 22 indicates the central axis of the regular cylinder. FIGS. 3(b) to (d) are examples wherein the raised surface is a curved surface composing a portion of the side wall of a regular cylinder. In FIGS. 3(b) to (d), the original regular cylinder is indicated by a dotted line. FIGS. 3(b) and (c) are examples wherein the cross-section is fan-shaped with a central angle θ (θ<180° in FIG. 3(b), and θ>180° in FIG. 3(c)).

Sample stages wherein the raised surface is a curved surface composing all or part of the side wall of a regular cylinder include sample stages wherein the cross-section has a shape formed from a circular arc and chord without the central axis 22, such as shown in FIG. 3(d).

By using a sample stage in which the raised surface is a curved surface composing all or part of the side wall of a regular cylinder, and applying the contact pressure of the sensor on the sample so as to be perpendicular to the central axis of the regular cylinder and pass through the central axis of the regular cylinder, it is possible to apply the contact pressure in the thickness direction of the sample.

Also, by using a sample stage in which the raised surface is a curved surface composing all or part of the side wall of a regular cylinder, and controlling the moving mechanism so that the sample stage rotates around the central axis of the regular cylinder, it is possible to measure a one-dimensional state quantity distribution of the sample while maintaining a constant height of the location of contact between the sample stage and sensor.

In addition, by using a sample stage in which the raised surface is a curved surface composing all or part of the side wall of a regular cylinder, and controlling the moving mechanism so that the sample stage rotates around the central axis of the regular cylinder while the sample stage moves parallel to the central axis of the regular cylinder, it is possible to measure a two-dimensional state quantity distribution of the sample while maintaining a constant height of the location of contact between the sample stage and sensor.

Figure 4:
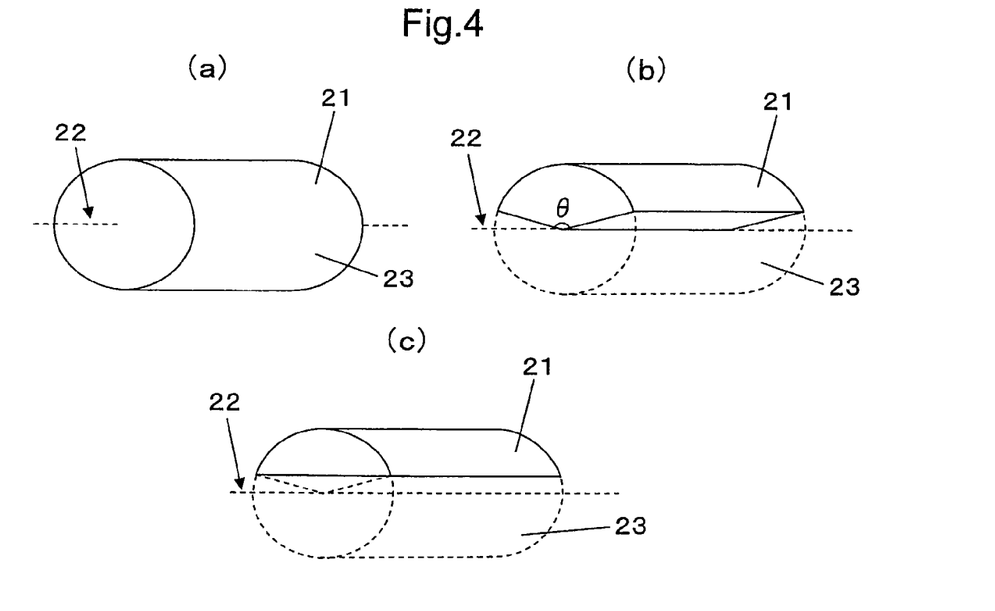
FIG. 4 is a set of diagrams showing examples wherein the raised surface is a curved surface composing all or part of the side wall of an elliptic cylinder.

FIG. 4 shows different examples of sample stages wherein the raised surface is a curved surface composing all or part of the walls of an elliptic cylinder. FIG. 4(a) is an example wherein the raised surface 21 is the curved surface composing the entirety of the side wall 23 of the elliptic cylinder. Numeral 22 indicates the central axis of the regular cylinder. FIGS. 4(b) and (c) are examples wherein the raised surface is a curved surface composing a portion of the side wall of an elliptic cylinder, the original elliptic cylinder being indicated by a dotted line. FIG. 4(b) is an example wherein the cross-section is approximately fan-shaped with central angle θ.

Sample stages wherein the raised surface is a curved surface composing all or part of the side wall of a regular cylinder also include sample stages wherein the cross-section has a shape formed from an elliptical arc and chord without the central axis 22, such as shown in FIG. 4(c).

By using a sample stage in which the raised surface is a curved surface composing all or part of the side wall of an elliptic cylinder, and the contact pressure of the sensor on the sample is applied so as to be perpendicular to the central axis of the elliptic cylinder and pass through the central axis of the elliptic cylinder, it is possible to apply the contact pressure in approximately the thickness direction of the sample.

Also, by using a sample stage in which the raised surface is a curved surface composing all or part of the side wall of an elliptic cylinder, and controlling the moving mechanism so that the sample stage rotates around the central axis of the elliptic cylinder, it is possible to measure a one-dimensional state quantity distribution of the sample while maintaining an approximately constant height of the location of contact between the sample stage and sensor.

In addition, by using a sample stage in which the raised surface is a curved surface composing all or part of the side wall of an elliptic cylinder, and controlling the moving mechanism so that the sample stage rotates around the central axis of the elliptic cylinder while the sample stage moves parallel to the central axis of the elliptic cylinder, it is possible to measure a two-dimensional state quantity distribution of the sample while maintaining an approximately constant height of the location of contact between the sample stage and sensor.

The size of the sample stage is not particularly restricted so long as it is a size allowing roughly the entire surface of the absorbent article to be placed thereon, and for example, with a sample stage as shown in FIG. 3 and FIG. 4, the diameter or long diameter of the cylinder may be approximately 7-13 cm while the height of the cylinder may be approximately 20-70 cm.

In the embodiment shown in FIG. 1, the moving mechanism 6 rotates the sample stage 3 around the central axis of the regular cylinder along direction A while moving the sample stage 3 parallel to the central axis, so that the state quantity distribution of the sample is measured, and the moving mechanism 6 does not control operation of the sensor 2.

However, the manner in which the moving mechanism controls movement is not particularly restricted so long as the state quantity distribution measuring apparatus can measure the state quantity distribution of the sample, but according to a different embodiment of the invention, for example, the moving mechanism can control movement of the sensor (that is, the moving mechanism does not control movement of the sample stage). According to yet another embodiment of the invention, the moving mechanism may control movement of both the sensor and sample stage, moving the sensor and sample stage in different directions, such as perpendicular directions. In this case, the moving mechanism may effect control so that the sample stage is rotated.

In the embodiments shown in FIG. 3 and FIG. 4, the moving mechanism preferably rotates the sample stage around the central axis of the cylinder to move the sensor with respect to the sample. This is because this can reduce variation in height at the location where the sample stage contacts the sensor during measurement of the state quantity distribution.

Also, the angle of rotation varies depending on the shape of the absorbent article sample and the size of the sample stage, and it is not particularly restricted but may be within about 180° or within about 90°, for example.

In the embodiments shown in FIG. 3 and FIG. 4, the moving mechanism preferably moves the sample stage parallel to the central axis of the cylinder to move the sensor with respect to the sample. The distance by which the moving mechanism moves the sample stage parallel to the central axis of the cylinder will vary depending on the shape of the absorbent article sample, and is not particularly restricted, but it may be about 0-40 cm, for example.

Figure 5:
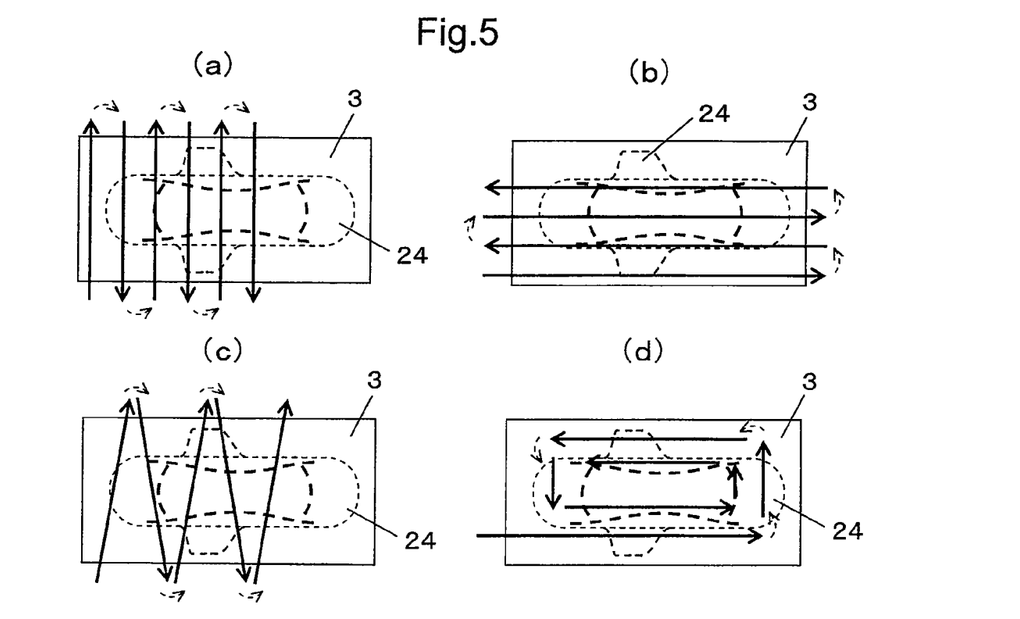
FIG. 5 is a set of diagrams showing movement examples in which a moving mechanism moves a sensor relative to a sample.

FIG. 5 shows movement examples in which a moving mechanism moves a sensor relative to a sample. FIG. 5 is a set of views from above the sample stage 3, with a sanitary napkin represented by a dotted line as the sample 4 on the sample stage 3. In FIG. 5, the arrows indicate relative movement of the sensor when the moving mechanism moves the sensor relative to the sample, the solid arrows representing scanning movement and the dotted arrows indicating non-scanning movement.

For convenience in FIG. 5, the lengthwise direction and lateral direction of the absorber are the x-axial direction and y-axial direction, respectively, with the point at the bottom left of the sample stage 3 in FIG. 5 being the zero point.

FIG. 5(a) is an example in which the cross-section of the absorbent article 24 in the direction orthogonal to the lengthwise direction is repeatedly scanned as the location in the lengthwise direction is varied. As a possible method for scanning as shown in FIG. 5(a): (i) the moving mechanism moves the sensor alone in the order indicated by the solid and dotted arrows in FIG. 5(a) (the moving mechanism does not move the sample stage), (ii) the moving mechanism moves the sample stage alone in the opposite order to that indicated by the solid and dotted arrows in FIG. 5(a) (the moving mechanism does not move the sensor), (iii) the moving mechanism rotates the sample stage to relatively move the sensor in the positive direction of the y-axis, while moving the sample stage in the negative direction of the x-axis to relatively move the sensor in positive direction of the x-axis, rotating the sample stage to relatively move the sensor in the negative direction of the y-axis, and moving the sample stage in the negative direction of the x-axis to relatively move the sensor in the positive direction of the x-axis, and then the procedure is repeated (the moving mechanism does not move the sensor).

Movement in the y-axial direction is accomplished by the sample stage, while movement in the x-axial direction is accomplished by the sensor.

FIG. 5(b) is an example in which the cross-section of the absorbent article 24 in the lengthwise direction is repeatedly scanned as the location in the direction orthogonal to the lengthwise direction is varied. As a possible method for scanning as shown in FIG. 5(b): (i) the moving mechanism moves the sensor alone as indicated by the solid and dotted arrows in FIG. 5(b) (the moving mechanism does not move the sample stage), (ii) the moving mechanism moves the sample stage alone in the opposite order to that indicated by the solid and dotted arrows in FIG. 5(b) (the moving mechanism does not move the sensor), (iii) the moving mechanism moves the sample stage in the negative direction of the x-axis to relatively move the sensor in the positive direction of the x-axis, while rotating the sample stage to relatively move the sensor in the positive direction of the y-axis and to relatively move the sensor in the negative direction of the x-axis, and then rotating the sample stage to relatively move the sensor in the positive direction of the y-axis, and this procedure is repeated (the sensor is not moved).

Movement in the y-axial direction is accomplished by the sample stage, while movement in the x-axial direction is accomplished by the sensor.

FIG. 5(c) is an example in which the cross-section of the absorbent article 24 in the oblique direction is repeatedly scanned as the location is varied. As a possible method for scanning as shown in FIG. 5(c): (i) the moving mechanism moves the sensor alone as indicated by the solid and dotted arrows in FIG. 5(c) (the moving mechanism does not move the sample stage), (ii) the moving mechanism moves the sample stage alone in the opposite order to that indicated by the solid and dotted arrows in FIG. 5(c) (the moving mechanism does not move the sensor), (iii) the moving mechanism moves the sample stage in a reciprocating rotational manner within a prescribed region while moving the sample stage at a constant speed in the negative direction of the x-axis (the moving mechanism does not move the sensor).

Also, the movement in the y-axial direction is accomplished by the sample stage while the movement in the x-axial direction is accomplished by the sensor, and these may be combined to achieve the movement illustrated in FIG. 5(c).

FIG. 5(d) is an example of scanning the absorbent article 24 from the outer edge toward the interior. As a possible method for scanning as shown in FIG. 5(d): (i) the moving mechanism moves the sensor alone as indicated by the solid and dotted arrows in FIG. 5(d) (the moving mechanism does not move the sample stage), (ii) the moving mechanism moves the sample stage alone in the opposite order to that indicated by the solid and dotted arrows in FIG. 5(d) (the moving mechanism does not move the sensor), (iii) the moving mechanism combines rotation in the y-axial direction and movement in the x-axial direction of the sample stage to relatively move the sensor as shown in FIG. 5(d) (the moving mechanism does not move the sensor).

Movement in the y-axial direction is accomplished by the sample stage, while movement in the x-axial direction is accomplished by the sensor.

In the embodiments illustrated in FIGS. 5(a) to (d), the moving mechanism preferably moves the sample stage alone. This will allow easy control of the contact pressure of the sensor against the sample using gravity.

The moving mechanism may be a motor, for example.

When the raised surface of the sample stage 3 shown in FIG. 5 is a curved surface composing all or part of the side wall of a cylinder, such as shown in FIG. 3 and FIG. 4, the x-axis may be in the direction parallel to the central axis of the cylinder while the y-axis may be in the direction created by rotation around the central axis of the cylinder.

In the state quantity distribution measuring apparatus shown in FIG. 1, the support mechanism is a balance. By using a balance as the support mechanism it is possible to maintain a constant contact pressure even when the sample to be measured has irregularities.

The support mechanism is not limited to a balance as shown in FIG. 5, so long as it can support a sensor such that the contact pressure on the sample is kept roughly constant. For example, the support mechanism may hold the sensor such that the contact pressure acts in the vertical direction and the sensor can be moved vertically.

Figure 6:
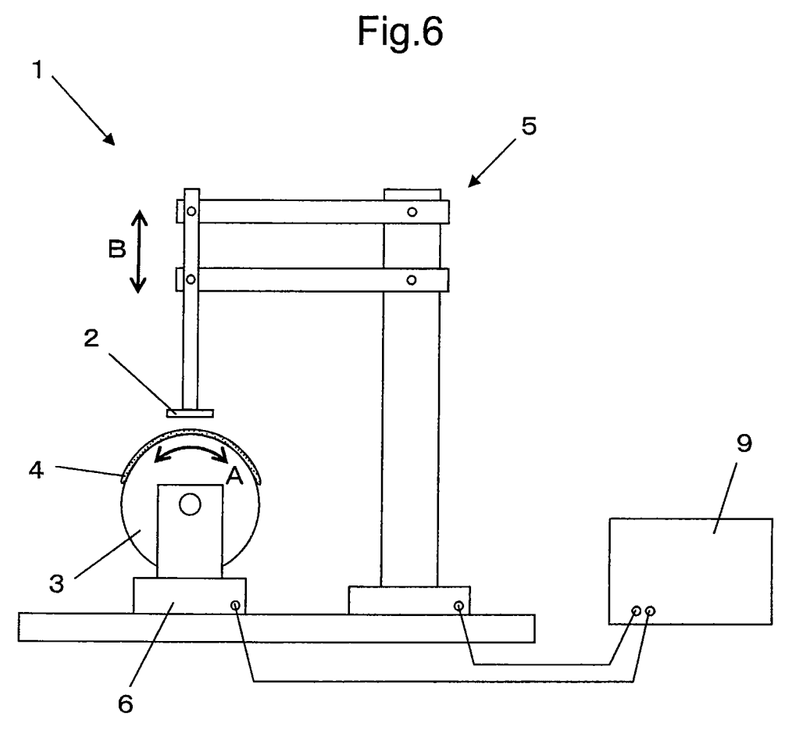
FIG. 6 is a diagram showing a different example of a support mechanism.

For example, when the sensor is not very heavy and there is no need to reduce the contact pressure of the sensor against the sample, there may be used a support mechanism 6 which does not have a weight on the side opposite the sensor, such as shown in FIG. 6.

The contact pressure of the sensor against the sample will differ depending on the sample to be measured and the type of sensor, and for example, it may be about 1-100 g/cm$^2$, preferably about 2-50 g/cm$^2$ and more preferably about 3-20 g/cm$^2$. For example, when a state quantity distribution is to be measured while reproducing body pressure that is applied to an absorbent article during wear, the contact pressure may be about 5-15 g/cm$^2$.

The measuring mechanism may be a computer, for example.

According to a different embodiment of the invention, the state quantity distribution measuring apparatus may further comprise a recording mechanism that records a state quantity measured by the sensor and positional information from the moving mechanism. The measuring mechanism and recording mechanism may also be the same computer.

With the state quantity distribution measuring apparatus, the state quantity distribution may be measured under constant conditions, such as after a fixed period of time, upon dropping artificial urine, artificial menstrual blood or the like onto an absorbent article as a sample and placing the absorbent article on the sample stage, but according to a different embodiment of the invention, the state quantity distribution measuring apparatus may further comprise a dropping mechanism which drops a test solution, such as artificial urine or artificial menstrual blood.

According to yet another embodiment of the invention, the dropping mechanism may be one capable of controlling the dropping rate, dropping volume, dropping frequency and dropping temperature for the test solution, in order to simulate actual urination or defecation.

According to yet another embodiment of the invention, the dropping mechanism may even be one wherein the dropping rate, dropping volume, dropping frequency and dropping temperature for the test solution are controlled by a computer. In this case, the computer may be the same one or a different one than the computer of the measuring mechanism and/or recording mechanism.

According to yet another embodiment of the invention, the sensor, support mechanism, moving mechanism, recording mechanism and dropping mechanism may be controlled by the same or different computers for fully automatic measurement of the state quantity distribution.

The state quantity distribution measuring apparatus may also have a display mechanism, such as a monitor or printer that displays the measurement results. The display mechanism will generally be connected to the measuring mechanism.

By providing the state quantity distribution measuring apparatus with a display mechanism, it is possible to represent the state quantity distribution of the sample in the form of a graph, for example.

Examples of graphs to be displayed by the display mechanism include (i) a three-dimensional graph, such as a three-dimensional contour line graph or three-dimensional vertical bar graph representing a state quantity distribution across the entire surface of the absorbent article, with the lengthwise direction of the absorbent article as the x-axis, the direction perpendicular to the lengthwise direction of the absorbent article as the y-axis, and a state quantity, such as moisture, humidity, temperature, heat flow rate or wind speed, of the absorbent article as the z-axis, and (ii) a two-dimensional graph, such as a line graph, bar graph or scatter plot representing a state quantity distribution for a cross-section of the absorbent article, where the x-axis is a direction perpendicular to the lengthwise direction of the absorbent article at some location in the lengthwise direction of the absorbent article, and the y-axis is the state quantity of the absorbent article.

Such graphical representation allows analysis of a state quantity distribution for an absorbent article sample, to determine, for example, that the area near the center of the absorber has a low moisture content while the moisture content is high at a location further ahead in the lengthwise direction, and that the high moisture content at that location may be unpleasant for the wearer.

The state quantity distribution measuring apparatus may further comprise a static-eliminating mechanism to eliminate static electricity in the sample or sensor, if the sensor is an electrical capacitance-type moisture sensor. Before measurement of the state quantity distribution of the sample, the sample may be electrically grounded to eliminate static electricity, for increased measuring precision.

EXAMPLES

The invention will now be explained in greater detail using examples and comparative examples, with the understanding that the invention is in no way limited by the examples.

Example 1

Reference samples 1-6 were fabricated with different moisture contents, by adding prescribed amounts of water to SILCOTT™ (Unicharm Corp.). The reference samples were then allowed to stand in a sealed state at 20° C. for 1 day.

Next, the state quantity distribution measuring apparatus shown in FIG. 1 was prepared.

Reference samples 1-6 were then each placed on the sample stage and the state quantity distribution measuring apparatus was used for measurement of the moisture contents. The contact pressure of the sensor for each sample was 8 g/cm$^2$.

Figure 7:
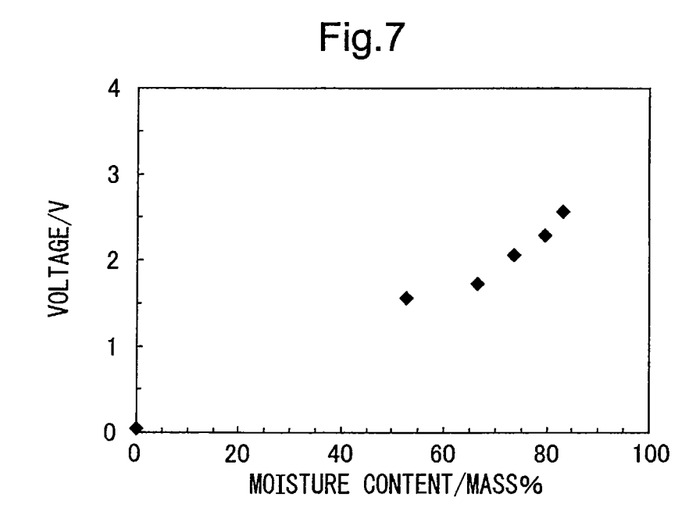
FIG. 7 is a graph showing the results of Example 1.

The results are shown in Table 1 and FIG. 7. Table 1 and FIG. 7 show the relationship between the moisture content (mass %) and the voltage (V) between the pair of electrodes.

TABLE 1

| Index | 1 | 2 | 3 | 4 | 5 | 6 |
|---|---|---|---|---|---|---|
| Moisture content (mass %) | 0.0 | 52.6 | 66.5 | 73.5 | 79.7 | 83.1 |
| Voltage (V) | 0.05 | 1.55 | 1.72 | 2.06 | 2.29 | 2.57 |

As is clear from Table 1 and FIG. 7, the state quantity distribution measuring apparatus allows quantitative evaluation of moisture content in a wide range.

Example 2

Each of Reference samples 1-6 was touched with the finger of multiple subjects and the state was evaluated on a 4-level scale of (i) dry, (ii) moist, (iii) wet, (iv) soaked.

The results are shown in Table 2.

TABLE 2

| Index | Moisture content (mass %) | Percentage (%) | | | |
|---|---|---|---|---|---|
| | | Dry | Moist | Wet | Soaked |
| 1 | 0.0 | 100 | 0 | 0 | 0 |
| 2 | 52.6 | 31 | 54 | 15 | 0 |
| 3 | 66.5 | 0 | 54 | 23 | 23 |
| 4 | 73.5 | 0 | 31 | 54 | 15 |
| 5 | 79.7 | 0 | 8 | 69 | 23 |
| 6 | 83.1 | 0 | 0 | 23 | 77 |

This allowed general categorization of "dry" for a moisture content of about. 0-50%, "moist" for a moisture content of about 50-70%, "wet" for a moisture content of about 70-80% and "soaked" for a moisture content of about 80-100%.

Based on the obtained data, the measurement results can also be used to draw a graph for visualization of the wetted state of an absorbent article, with a dry condition represented by white and a soaked condition represented by blue, instead of the moisture content.

Example 3

As a sample there was prepared Sofy Bodyfit™, Regular daily use, with wings (product of Unicharm Corp.). At the center of the sample (the center in the lengthwise direction and the center in the direction perpendicular to the lengthwise direction) there was dropped 6 mL of artificial menstrual blood.

Next, the sample was placed on the sample stage of the state quantity distribution measuring apparatus shown in FIG. 1, an insulating film composed of polyvinylidene chloride was set on the sample, and a sensor was placed on the sample, sandwiching the insulating film therebetween. The contact pressure of the sensor was 8 g/cm$^2$.

One minute after dropping the artificial menstrual blood, the moisture content distribution of the sample was measured as shown in FIG. 5(a). Measurement was performed with the x-axis as the direction perpendicular to the lengthwise direction of the sample (positive being the right side of the sample) the y-axis as the lengthwise direction of the sample (positive being the front side of the sample), and the center as the zero point, measuring the electrostatic capacity at 7 points at 5 mm spacings, from x=−15 to +15 (mm) at y=+6 (mm), and then at y=+3 (mm). Next, measurement was performed in the same manner at y=0, −3 and −6 (mm).

Figure 9:
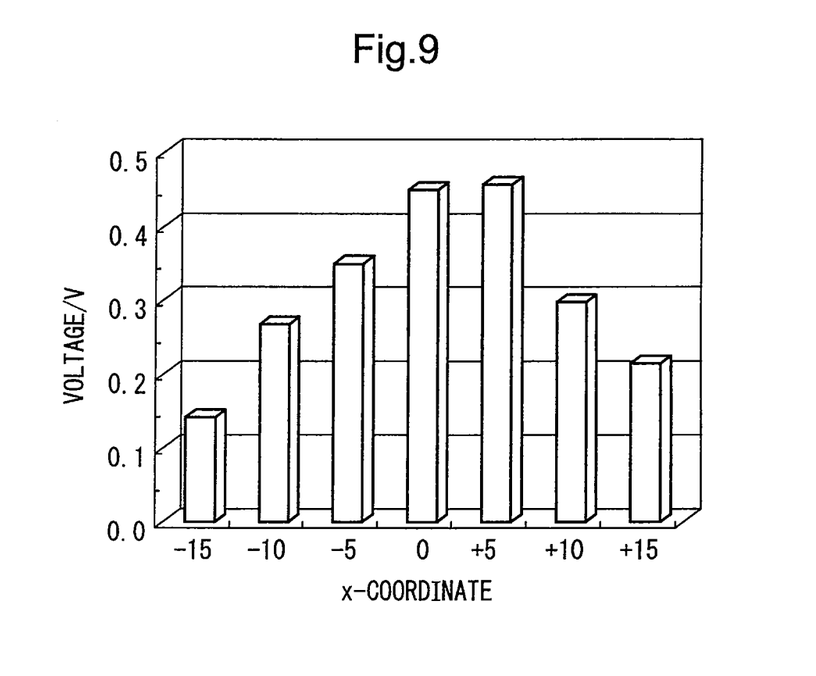
FIG. 9 is a graph showing the results of Example 3.

FIG. 9 shows a bar graph of electrostatic capacity distribution in the direction perpendicular to the lengthwise direction of the sample, with y=0. The electrostatic capacity is represented as the measured voltage.

Figure 10:
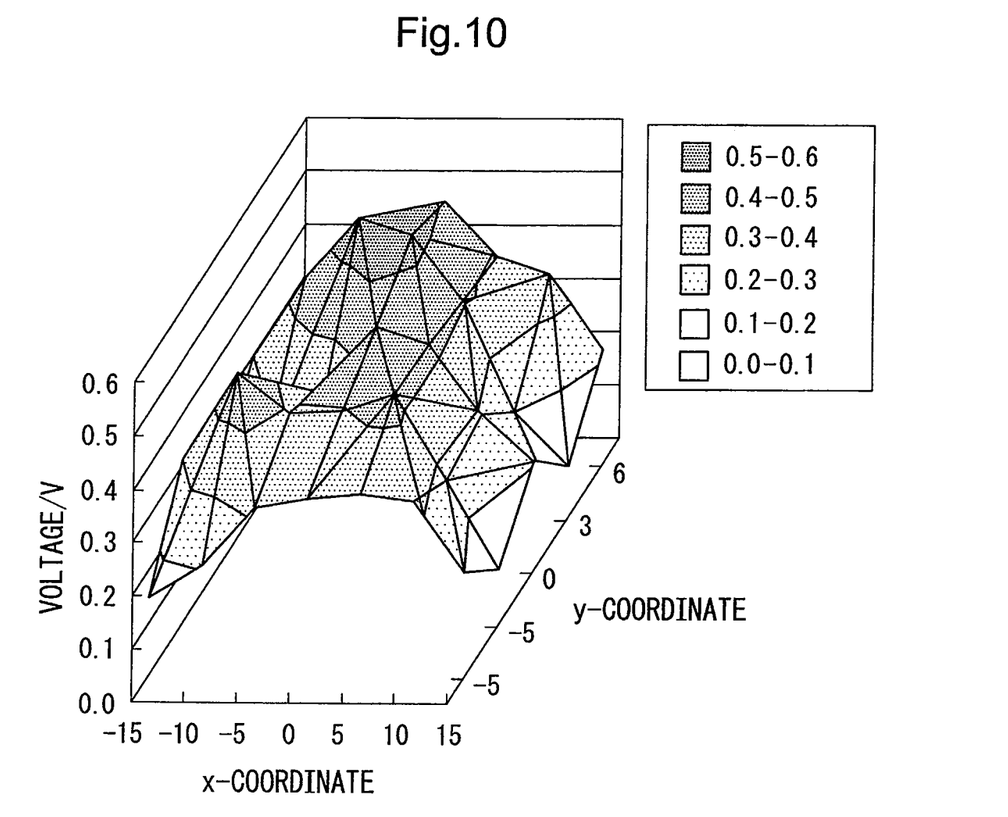
FIG. 10 is a graph showing the results of Example 3.

FIG. 10 shows a three-dimensional contour line graph of electrostatic capacity distribution in the sample.

REFERENCES SIGNS LIST

1 State quantity distribution measuring apparatus
2 Sensor
3 Sample stage
4 Sample
5 Support mechanism
6 Moving mechanism
7 Insulating film
8 Weight
9 Measuring mechanism
10a, 10b Electrodes
11 Electrode-supporting member
21 Raised surface
22 Central axis
23 Side wall
24 Absorbent article
25 Absorbent sheet
26 Weigh

The invention claimed is:

1. A state quantity distribution measuring apparatus, comprising:
   a sensor selected from the group consisting of a moisture sensor, a humidity sensor, a temperature sensor, a heat flow rate sensor and a wind speed sensor, which measures a state quantity of a sample,
   a sample stage on which a sample to be measured, consisting of an absorbent article, is placed, and which has a raised surface for placing the sample thereon,
   a support mechanism which supports the sensor such that the contact pressure of the sensor with respect to the sample is essentially constant,
   a moving mechanism which moves either or both the sensor and the sample so that the sensor moves relative to the sample, and
   a measuring mechanism that measures a state quantity of the sample at multiple locations using the sensor, while moving the sensor relative to the sample by controlling the moving mechanism, thereby measuring the state quantity distribution of the sample,
   wherein the sensor is an electrical capacitance-type moisture sensor, and the state quantity distribution measuring apparatus further comprises an insulating film separate from the sensor and situated between the sensor and the sample, for covering the sample.

2. The state quantity distribution measuring apparatus according to claim 1, wherein the sensor has a pair of electrodes situated parallel across a predetermined spacing.

3. The state quantity distribution measuring apparatus according to claim 1, wherein the raised surface of the sample stage is a curved surface forming all or part of the side wall of a cylinder.

4. The state quantity distribution measuring apparatus according to claim 3, wherein the moving mechanism rotates the sample stage around the central axis of the cylinder, thereby moving the sensor relative to the sample.

5. The state quantity distribution measuring apparatus according to claim 3, wherein the moving mechanism moves the sample stage parallel to the central axis of the cylinder, thereby moving the sensor relative to the sample.

6. The state quantity distribution measuring apparatus according to claim 1, wherein the support mechanism holds the sensor such that contact pressure acts in the vertical direction and the sensor is capable of up-down movement.

7. The state quantity distribution measuring apparatus according to claim 6, wherein the support mechanism is a balance.

8. The state quantity distribution measuring apparatus according to claim 1, further having a display mechanism that displays measurement results.

9. A method of measuring the state quantity distribution of a sample, comprising the steps of:
   (a) providing a state quantity distribution measuring apparatus comprising the following:
      (i) an electrical capacitance-type moisture sensor which measures the moisture content of a sample, (ii) a sample stage on which a sample to be measured, consisting of an absorbent article, is placed, and which has a raised surface for placing the sample thereon, (iii) a support mechanism which supports the sensor such that the contact pressure of the sensor with respect to the sample is essentially constant, (iv) a moving mechanism which moves either or both the sensor and the sample so that the sensor moves relative to the sample, (v) a measuring mechanism, and (vi) an insulating film separate from the sensor and situated between the sensor and the sample, for covering of the sample, (b) placing the sample on the raised surface of the sample stage, (c) setting the insulating film on the sample, (d) setting the sensor on the sample so as to sandwich the insulating film therebetween, and (e) measuring the state quantity distribution of the sample, in which the measuring mechanism measures a state quantity of the sample at multiple locations using the sensor, while moving the sensor relative to the sample by controlling the moving mechanism.

10. The method according to claim 9, wherein the state quantity distribution measuring apparatus further comprises a display mechanism that displays measurement results.

\* \* \* \* \*